US00PP22432P2

(12) United States Plant Patent
Levac

(10) Patent No.: US PP22,432 P2
(45) Date of Patent: Jan. 3, 2012

(54) ***SPIRAEA* PLANT NAMED 'DENISTAR'**

(50) Latin Name: *Spiraea×bumalda*
Varietal Denomination: Denistar

(76) Inventor: Denis Levac, Ste-Adele (CA)

( * ) Notice: Subject to any disclaimer, the term of this patent is extended or adjusted under 35 U.S.C. 154(b) by 0 days.

(21) Appl. No.: 12/800,253

(22) Filed: May 12, 2010

(51) Int. Cl.
*A01H 5/00* (2006.01)

(52) U.S. Cl. ..... Plt./226

(58) Field of Classification Search ..... Plt./226
See application file for complete search history.

(56) References Cited

OTHER PUBLICATIONS

Upov-rom Plant Variety Database 2011/01. Citation for *Spiraea* 'Denistar', one page.*

* cited by examiner

*Primary Examiner* — June Hwu
(74) *Attorney, Agent, or Firm* — Penny J. Aguirre

(57) ABSTRACT

A new cultivar of *Spiraea×bumalda* 'Denistar', characterized by its foliage that emerges scarlet red new growth foliage and changes to dark fir green when it matures and bronze in fall, its dark pink flowers, its small, compact plant habit, its vigorous growth habit, and its hardiness in U.S.D.A. Zones 3 to 8.

2 Drawing Sheets

Botanical classification: *Spiraea×bumalda*.
Variety denomination: 'Denistar'.

BACKGROUND OF THE INVENTION

The present invention relates to a new and distinct cultivar of *Spiraea*, botanically known as *Spiraea×bumalda* 'Denistar' and will be referred to hereafter by its cultivar name, 'Denistar'. 'Denistar' is a new variety of bridal-wreath spirea for landscape use.

The inventor discovered 'Denistar' as a naturally occurring branch mutation of *Spiraea×bumalda* 'Froebelii' (not patented) in 2004 growing in a garden near Montreal, Quebec, Canada.

Asexual reproduction of the new cultivar was first accomplished by the Inventor using softwood stem cuttings in 2004 in Quebec, Canada. The characteristics of this cultivar have been determined both by stem cuttings and tissue culture to be stable and are reproduced true to type in successive generations.

SUMMARY OF THE INVENTION

The following traits have been repeatedly observed and represent the characteristics of the new cultivar as grown outdoors in a test gardens for three years in Quebec, Canada and St. Paul, Minn. These attributes in combination distinguish 'Denistar' as a unique cultivar of *Spiraea*.

1. 'Denistar' has foliage with unique coloration; the new growth is scarlet red, changing to dark green as it matures and then changing to bronze in fall.
2. 'Denistar' blooms profusely with dark pink flowers appearing in mid-June and blooming continually for up to 15 weeks.
3. 'Denistar' has a small, compact, plant habit.
4. 'Denistar' is hardy in U.S.D.A. Zones 3 to 8.

'Denistar' is unique in comparisons to other cultivars of *Spiraea* known to the Inventor. *Spiraea×bumalda* 'Froebelli', the parent plant, has new growth foliage that emerges purplish and then turns medium green and has no significant fall color. 'Froebelli' also differs from 'Denistar' in having a larger plant habit. 'Denistar' can also be compared to the cultivar 'Monhub' (U.S. Plant Pat. No. 5,834), which is similar in having foliage with reddish new growth and bronze fall color. 'Monhub' differs from 'Denistar' in having mature foliage that is bright yellow-green in color.

BRIEF DESCRIPTION OF THE DRAWING

The accompanying colored photographs illustrate the overall appearance and distinct characteristics of the new *Spiraea*. The plant shown in the photographs was taken of a plant 3 years in age as grown in a trial garden in St. Paul, Minn.

The photograph in FIG. 1 illustrates the compact habit and the scarlet red coloration of the new growth of 'Denistar'.

Figure 1:
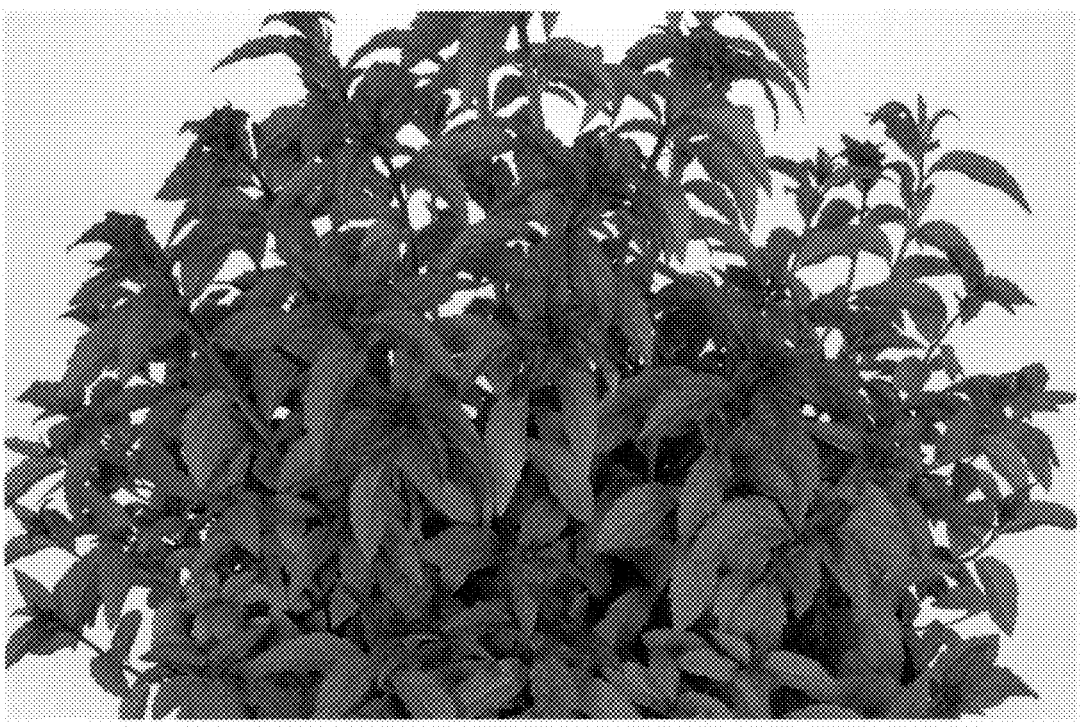
Figure 2:
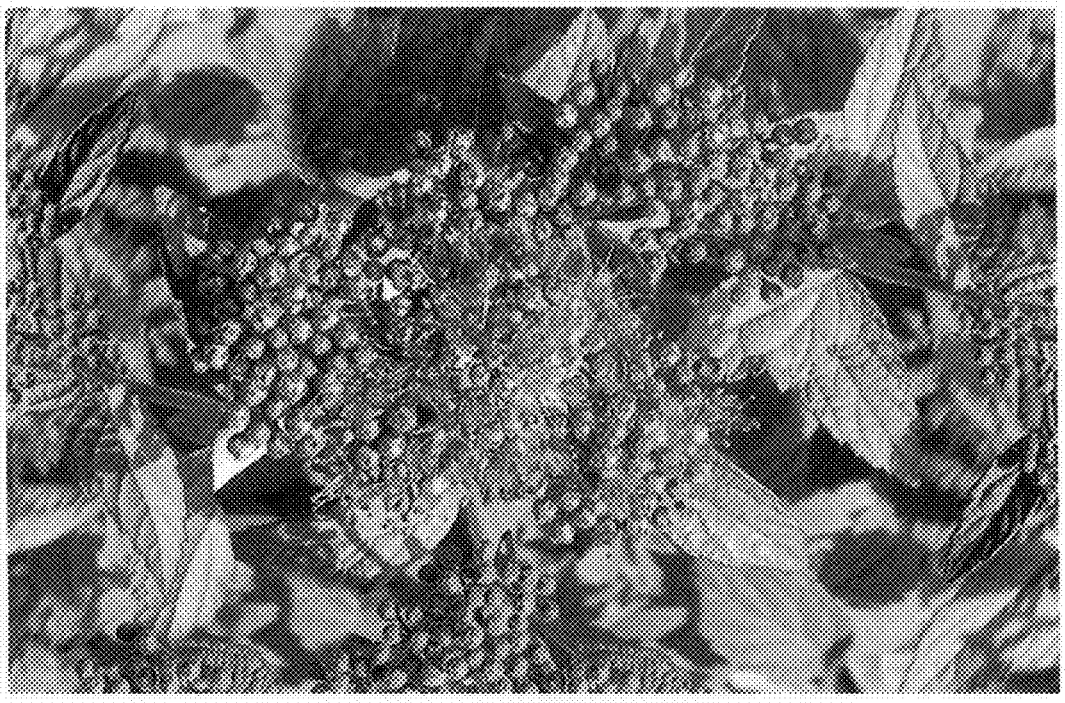

The photograph in FIG. 2 provides a close-up view of the flower clusters of 'Denistar'.

Figure 3:
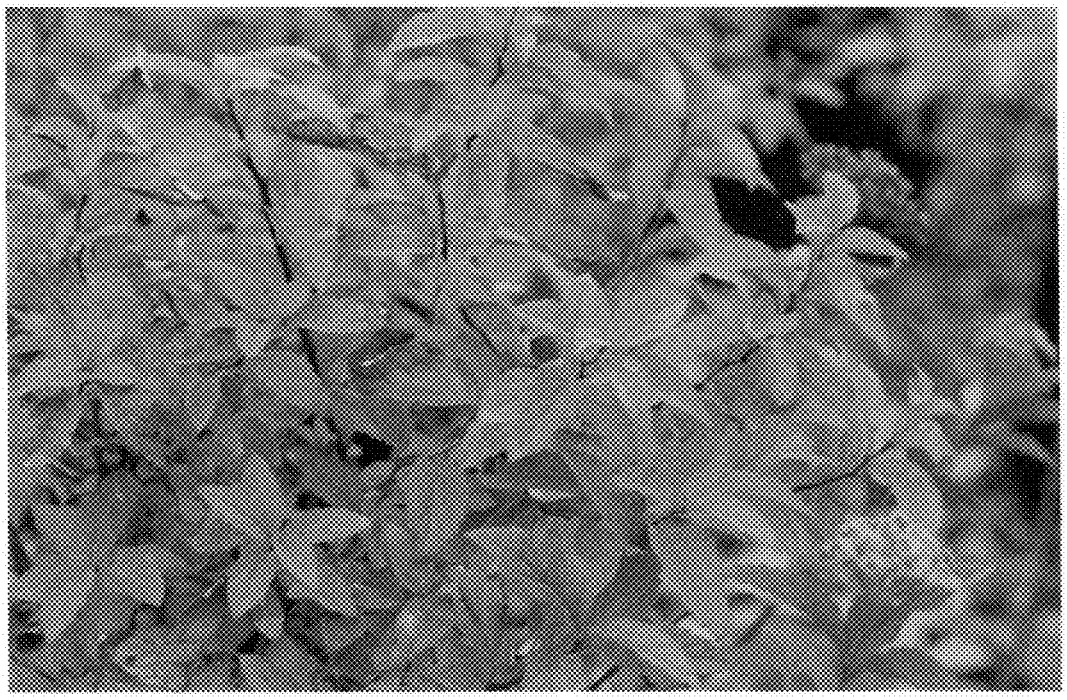

The photograph in FIG. 3 provides a close-up view of the bronze foliage of 'Denistar' in fall. The colors in the photographs are as close as possible with the digital photography techniques available, the color values cited in the detailed botanical description accurately describe the colors of the new *Spiraea*.

DETAILED BOTANICAL DESCRIPTION

The following is a detailed description of the new cultivar as grown outdoors in in a trial garden in Quebec, Canada for five years with the detailed botanical data collected from a plant 2 years in age as grown outdoors in a 2-gallon container in St. Paul, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:.

*Blooming period.*—Initiating in mid-June and continuing for up to 15 weeks.

*Plant type.*—Deciduous shrub.

*Plant habit.*—Compact, mounded.

*Height and spread.*—Reaches about 2 to 3 feet in height and about 3 to 4 feet in width.

*Hardiness.*—U.S.D.A. Zones 3 to 8.

*Diseases and pests.*—No susceptibility or resistance to diseases or pests has been observed.

*Root description.*—Fibrous.

Growth and propagation:

*Propagation.*—Softwood stem cuttings.

*Growth rate.*—Vigorous.

Stem description:

*Shape.*—Slightly oval.

*Stem color.*—New growth; 144B becoming 174A as it matures, mature wood; a blend between N199D and 165D with striations of 200B.

*Stem size.*—Main stems; at least 18 cm in length and an average of 4 cm in width, lateral branches; an average of 14 cm in length and 1.5 mm in width.

*Stem surface.*—New growth; weakly pubescent, mature wood; bark-like but fairly smooth with fine striations.

*Internode length.*—Average of 2 cm.

*Branching.*—An average of 4 lateral branches per main stem, readily produces additional branches if pruned.

Foliage description:

*Leaf shape.*—Elliptic to broadly ovate.

*Leaf division.*—Simple.

*Leaf base.*—Cuneate.

*Leaf apex.*—Acute.

*Leaf fragrance.*—None.

*Leaflet venation.*—Not prominent, pinnate, vein coloration matches leaf coloration.

*Leaflet margins.*—Serrated with mucronulate apex on each serration.

*Leaf arrangement.*—Alternate.

*Leaf attachment.*—Petiolate.

*Leaf surface.*—Glabrous and semi-glossy on upper surface and very finely puberulent and dull on lower surface.

*Leaf size.*—Average of 3.6 cm in length and 1.4 cm in width.

*Leaf quantity.*—About 12 on a branch 13 cm in length.

*Leaf color.*—Upper and lower surface new leaves, 60B to 61A; upper surface mature leaves, 137C, lower surface mature leaves; 138A, upper and lower surface of leaves in fall; 179C at base to N172B towards apex.

*Petioles.*—About 3 mm in length, 1.2 mm in width, 144B in color, glabrous surface.

*Stipules.*—Absent.

Inflorescence description:

*Inflorescence type.*—Dense umbellate corymbs, present at terminal of lateral branches.

*Inflorescence size.*—About 3.5 cm in diameter and 1.5 cm in depth.

*Peduncles.*—About 1.5 cm in length and 0.9 mm in width, 144A in color, pubescent surface.

*Pedicels.*—An average of 4 mm in length and 0.5 mm in width, 144B in color, pubescent surface.

*Flower buds.*—Globose in shape, 2 mm in depth and diameter, 59C in color with sepal portion 137C.

*Flower fragrance.*—Absent.

*Persistence of flowers.*—Calyx persistent.

*Flower quantity.*—Average of 30 per inflorescence, average of 180 flowers per plant grown in a 2-gallon container.

*Lastingness of flowers.*—Each inflorescence lasts about 10 days with individual flowers lasting about 2 days.

*Flower type.*—Rotate with numerous extended stamens.

*Flower aspect.*—Inflorescence held upright on stem terminus.

*Flower size.*—About 6 mm in diameter.

*Petals.*—5, about 2 mm in length and width, un-fused, orbicular in shape, rounded base, rounded apex, glabrous surface, 72A in color when opening, changing to 84B and fading to 84C, not persistent.

*Calyx.*—Cone-shaped with flared tips, about 3 mm in width and 1.5 mm in depth.

*Sepals.*—5, tips are about 1.5 mm in width and depth, fused base, ovate in shape, entire margins with fine hairs, acute apex 144A in color on lower surface with upper surface 144C blending with 72A, pubescent surface.

Reproductive organs:

*Pistils.*—5, style; 2 mm in length and N78B in color, stigmas; 0.3 mm in diameter, 160C in color, ovaries; superior; oblong in shape, 0.7 mm in length and 0.2 in width, 154C in color.

*Stamens.*—20, showy filaments; up to 6 mm in length and 84C in color, anthers; 0.3 mm in diameter, about 59C becoming 200A in color, pollen; moderate in quantity, 155D in color.

*Fruit and seed.*—Capsules; about 3 mm in length, 1 mm in width, and N199C in color, seed; ovate and alate, <0.5 mm in diameter, no seed development was observed.

It is claimed:

1. A new and distinct cultivar of *Spiraea* plant named 'Denistar' as herein illustrated and described.

* * * * *